(12) United States Patent
Barlag et al.

(10) Patent No.: US 7,591,938 B2
(45) Date of Patent: Sep. 22, 2009

(54) METHOD AND DEVICE FOR TRANSPORTING OR BINDING-SPECIFIC SEPARATION OF ELECTRICALLY CHARGED MOLECULES

(75) Inventors: Heike Barlag, Nürnberg (DE); Walter Gumbrecht, Herzogenaurach (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 869 days.

(21) Appl. No.: 10/537,248
(22) PCT Filed: Nov. 28, 2003
(86) PCT No.: PCT/DE03/03938

§ 371 (c)(1),
(2), (4) Date: Jun. 1, 2005

(87) PCT Pub. No.: WO2004/051275

PCT Pub. Date: Jun. 17, 2004

(65) Prior Publication Data

US 2006/0086625 A1    Apr. 27, 2006

(30) Foreign Application Priority Data

Dec. 2, 2002 (DE) ................. 102 56 415

(51) Int. Cl.
G01N 27/26 (2006.01)
G01N 33/487 (2006.01)
G01F 1/64 (2006.01)
(52) U.S. Cl. ............... 205/775; 204/450; 204/409; 204/410; 204/411
(58) Field of Classification Search .......... 204/450, 204/600, 548, 409–411; 435/6, 7.1, 91.1
See application file for complete search history.

(56) References Cited

U.S. PATENT DOCUMENTS 4,589,958 A * 5/1986 Alexander et al. ..... 205/780.05
5,605,662 A 2/1997 Heller et al.

FOREIGN PATENT DOCUMENTS

WO    WO 02/063041 A1    8/2002

OTHER PUBLICATIONS

Potentiometric Monitoring of Proteins, Hitchman M and Nyasulu F, J. Chem. Soc., Faraday Trans. 1, 1986, 82, 1223-1236.*
The reduction of Cu(II) complexes of histidine and histidyl peptides at mercury electrodes, Bilewicz, J. Electroanal. Chem, 267, 1989, 231-241.*

* cited by examiner

*Primary Examiner*—Alexa D Neckel
*Assistant Examiner*—G. K.
(74) *Attorney, Agent, or Firm*—Harness, Dickey & Pierce, P.L.C.

(57) ABSTRACT

Electrically charged molecules need to be transported in order to create a DNA sensor. The following measures are undertaken: base metals are introduced into a solution as a positive ion; negatively charged molecules are transported in an opposite direction and are enriched in the vicinity of the measuring electrodes. Binding-specific separation of the charged molecules can be achieved by forming metal layers on the measuring electrodes by depositing metal ions from the solution when a suitable potential is selected. Target DNA can more particularly be introduced into the vicinity of the catcher molecules on the measuring electrodes and non-specifically bound DNA can be removed. According to the associated device, the electrode arrangement may be associated with a sacrificial electrode made of more base metal than the material of the measuring electrodes. The measuring electrodes in particular may be made of noble metal, preferably gold, and the sacrificial electrode may be made of copper.

27 Claims, 5 Drawing Sheets

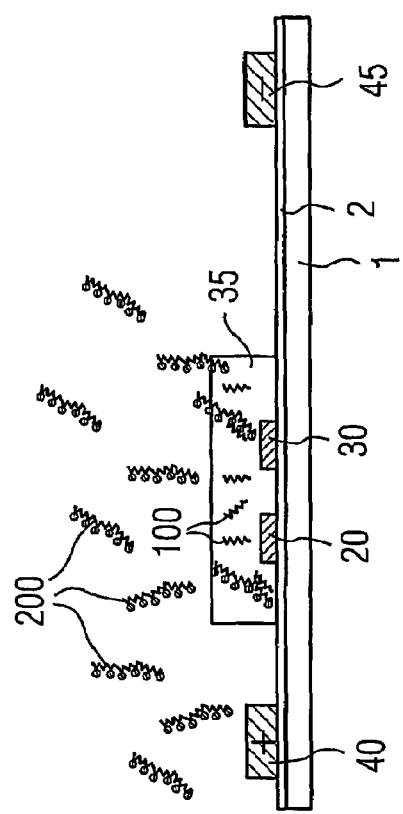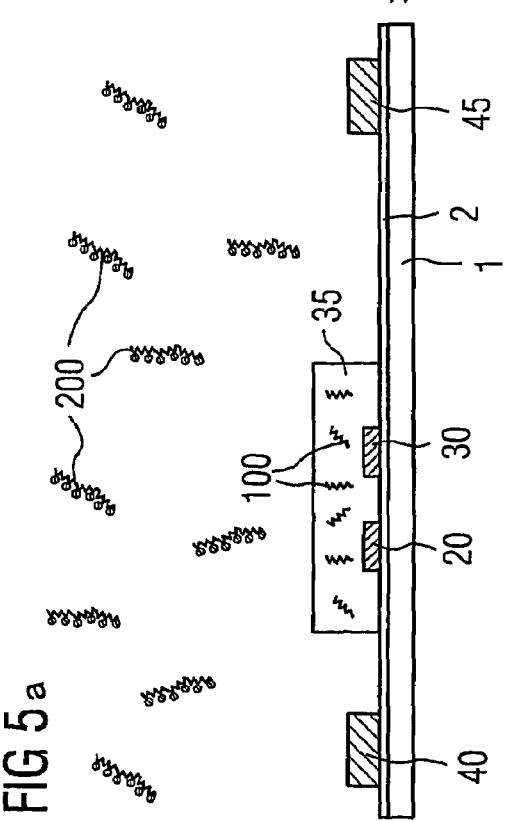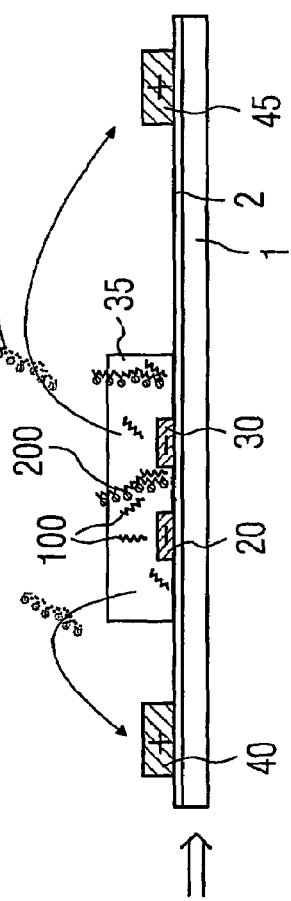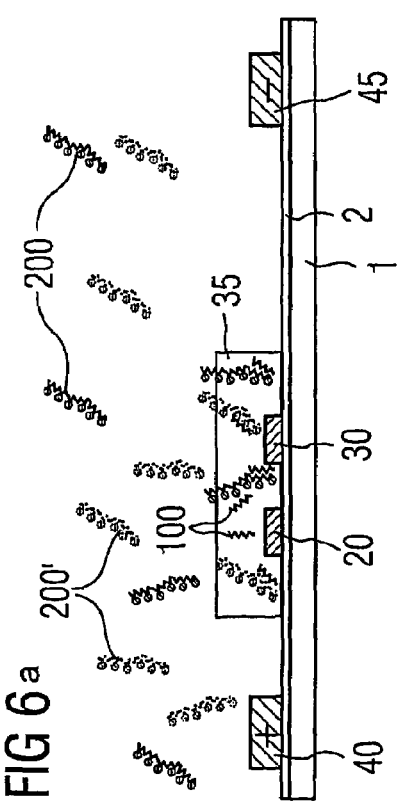

US 7,591,938 B2

METHOD AND DEVICE FOR TRANSPORTING OR BINDING-SPECIFIC SEPARATION OF ELECTRICALLY CHARGED MOLECULES

This application is the national phase under 35 U.S.C. § 371 of PCT International Application No. PCT/DE2003/003938 which has an International filing date of Nov. 28, 2003, which designated the United States of America and which claims priority on German Patent Application number DE 102 56 415.9 filed Dec. 2, 2002, the entire contents of which are hereby incorporated herein by reference.

FIELD OF THE INVENTION

The invention generally relates to a method for transporting or binding-specific separation of electrically charged molecules in an aqueous solution, in particular during the operation of a DNA sensor with a redox cycling process between measuring electrodes. The invention additionally generally relates to the associated devices.

BACKGROUND

The transporting of charged particles in an electric field (migration) plays an important part in numerous methods of molecular biology. The migration velocity v of the charged particles in the liquid medium is in this case proportional to the field strength E and the ion charge Q and inversely proportional to the particle radius r and the viscosity η of the suspension. The following results for the velocity v:

$$v = QE/6\pi r \eta \quad (1)$$

During electrophoresis, by way of example, biomolecules, i.e primarily proteins and DNA, which differ with regard to their size and/or charge are separated from one another. The presence of other mobile charged particles is to be avoided in certain forms of electrophoretic separation (e.g. isoelectric focusing) since otherwise the charge transport is undertaken partly or wholly by these particles and not by the molecules to be separated. Therefore, amino acids that have their isoelectric point at the desired pH value are often used as a buffer. That is to say that, at the pH value set, the buffer molecules themselves have no net charge and are therefore not subject to migration.

Electric fields are also used in the transporting of charged molecules, e.g. in order to increase or to decrease the concentration at a specific location. Particularly in the case of microsensors, e.g. for DNA analysis, it is possible to increase the sensitivity if the DNA fragments (target molecules) to be detected are concentrated at the location of the capture molecules (sensor surface). The number of capture/target molecule bonds thus increases in accordance with the law of mass action. In any event, however, during such a reaction not only are capture/target molecule pairs formed which match one another exactly but also those whose sequence do not correspond to one another exactly at some sites (mismatches).

Since the magnitude of the binding energy decreases with the number of non-corresponding bases, those bonds which have a specific number of mismatches can be separated again selectively by the application of appropriate forces (stringency treatment). As force, it is possible here for an electric field to take effect which has an opposite polarity in contrast to the first process, the concentration of the molecules.

A prerequisite for transporting charged particles in the electric field is a field gradient that has a strictly monotonic profile within the electrolyte or the transport path. That is to say that the field gradient must not change its sign and must not become zero. The application of an arbitrary voltage is not necessarily sufficient for this purpose for aqueous systems.

In the absence of a chemical reaction before the electrodes, the voltage drops across the electrochemical double layer and the field gradient between the electrodes becomes zero. However, if a reduction or oxidation reaction takes place at the electrodes, the double layer before the electrodes is depolarized and the electric field has a strictly monotonic profile within the electrolyte. Ion transport in the aqueous electrolyte is the consequence.

A method that is frequently employed for generating such electric fields in aqueous systems is application of the decomposition voltage of water. In this case, oxygen is evolved at the anode and hydrogen at the cathode. In the experimental implementation, care must be taken to ensure that the gases, and in particular their free radical precursors do not come into contact with the molecules to be examined, since the latter would otherwise be altered chemically. In macroscopic systems, this is done by separating the electrolyte spaces directly before the electrodes from the electrolyte space between the electrodes, e.g. by means of diaphragms. This solution is problematic for microsensors since diaphragms are not practicable.

One possibility for electrophoresis in microsystems resides in introducing so-called permeation layers made of hydrophilic polymer before the electrodes, in respect of which reference is made to U.S. Pat. No. 5,605,662 A. The mobility of reaction products of the electrolysis of water and the DNA to be transported is severely inhibited in this layer, so that an intermixing virtually does not take place. The charge transport in the permeation layer is undertaken by smaller ions.

Although the known method is practicable, the introduction of new polymer layers makes the production of the microsensor chip significantly more complicated and thus more expensive.

SUMMARY

An object of an embodiment of the invention to specify a suitable method for transporting the charged molecules via an electric field, in the case of which no evolution of hydrogen or oxygen occurs at the electrode. In particular, with utilization of the electrophoresis method, a corresponding device may be created that manages with standard materials and layers of chip production.

In the case of the device according to an embodiment of the invention, a construction that is identical, in principle, can be used optionally to perform the method according to at least one embodiment of the invention. In this case, it is also advantageously possible to combine two methods with one another, for example cyclically.

In the application of the electrophoresis method, an embodiment of the invention makes use of the fact that, in addition to the electrolysis of water, other reactions can also be used for generating the electric field in the analyte solution. An embodiment of the invention proposes a metal/metal ion complex, e.g. copper/copper-histidine complex, as a depolarizer before the electrodes. In the event of positive polarization of a copper-coated electrode for the purpose of concentrating negatively charged ions, oxygen is not then evolved; instead, the copper goes into solution as ion. If a complexing agent for the metal, e.g. histidine for copper is present there, then the metal iron remains stably in solution. Since e.g. the copper-histidine complex is very stable, the concentration of the free copper ions remains very small and virtually constant. An influence of the copper ions on the DNA hybridization is thereby avoided.

If the electrode is intended to be negatively polarized in order e.g. to increase the selectivity of the capture/target molecule binding (stringency treatment), i.e. to remove non-specifically bound, non-complementary sample DNA from the capture DNA, the metal ions are reduced in the presence of a metal ion complex of a sufficiently noble metal, e.g. copper. Further, they are deposited in the process on the electrodes (in this case the measuring electrode). Evolution of hydrogen is thereby avoided.

The complexing agent for the metal ion may, under certain circumstances, also serve simultaneously as a buffer. Histidine is used for example as a buffer at pH=7. The copper deposited on the measuring electrodes can be removed in a washing step by renewed application of negative potential. A repulsion of the target molecules is prevented by using a washing solution with high ionic strength, so that only e.g. copper in the form of $Cu^{2+}$ ions is removed, but the target DNA is not moved.

An advantage of an electrophoresis method based on metal/metal ion complex resides in the lower voltage required for generating the electric field. It is lower than the electrolysis voltage of water, so that the aggressive products of the electrolysis of water cannot arise. A separation of electrolysis space and electrophoresis space thus becomes unnecessary. The generated field nevertheless suffices to transport the desired molecules in the analyte.

Copper is already used nowadays for interconnects and may be used in the future as an electrode material for sensor applications or Microsystems engineering applications such as micro-electrophoresis. In the production of such a microsystem it is therefore possible to have recourse to cost-effective standard methods of semiconductor technology.

BRIEF DESCRIPTION OF THE DRAWINGS

Further details and advantages of the invention emerge from the following description of figures of example embodiments with reference to the drawings in conjunction with the patent claims. In the figures:

FIGS. 5a and 5b show, in the case of arrangements in accordance with FIG. 3, in method terms, the enrichment of target molecules from low to high concentration, FIGS. 6a and 6b show, in method terms, a situation in accordance with FIG. 5b, in which, however, non-specific, i.e. non-complementary sample DNA are also present, which are subjected to a so-called stringency treatment.

The figures will be described together in part.

DETAILED DESCRIPTION OF THE EXAMPLE EMBODIMENTS

Figure 1:
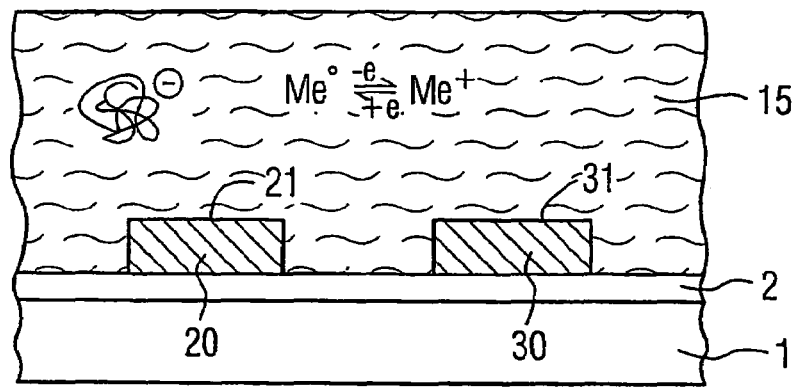
FIG. 1 shows a basic construction for carrying out the method according to an embodiment of the invention.

The basic construction of a general arrangement for carrying out biochemical measurements can be seen from FIG. 1.

Element 1 designates a planar substrate, e.g. made of silicon, on which a thin insulator layer 2, e.g. made of silicon oxide ($SiO_2$), is applied. Two measuring electrodes 20 and 30, which preferably include noble metal, in particular gold, are situated on this arrangement. The entire measuring arrangement is in contact with an aqueous solution 15.

The aqueous solution 15 contains negatively charged macromolecules. This is illustrated by the bundle structure in FIG. 1, and which are designated specifically by 200, 200' further below in FIG. 5. The negatively charged molecules are intended to be transported to the measuring electrodes 20, 30 and are also referred to hereinafter as target molecules. In the case of a DNA analysis, the target molecules of the DNA to be examined. By way of capture molecules that can be immobilized e.g. in a hydrogel layer 35, it is possible to attach the target DNA for the purpose of measurement in the vicinity of the electrodes 20, 30.

In the aqueous solution 15 there is furthermore present a material which is resistant in the aqueous solution and more electronegative than the metal of the measuring electrodes. In the most general case, the material is a metal/metal ion (Me/$Me^+$) combination, for example $Cu/Cu^{2+}$. Thus, in accordance with the predetermined potential conditions, either metallic copper $Cu^o$ is dissolved with two electrons being released or copper(II) ions $Cu^{2+}$ can be deposited with two electrons being taken up, in which case the following holds true:

$$Cu^o \Longleftrightarrow Cu^{++} + 2e \qquad (2)$$

In the case of the arrangement in accordance with FIG. 5, in the case of a copper electrode as sacrificial anode 40, $Cu^{2+}$ can go into solution as a result of a positive potential being applied. As a result, the negative target molecules 200 are moved there to the copper electrode 40 and accumulate in the vicinity thereof and thus also in the region of the measuring electrodes 20, 30.

If, with the presence of $Cu^{2+}$ ions in the aqueous solution, a suitable negative potential is applied to the measuring electrodes 20, 30 in accordance with FIG. 6, both capture molecule/target DNA bonds break which have a reduced binding strength on account of incomplete complementarity. At the same time, copper(II) ions ($Cu^{2+}$) are reduced to form metallic copper ($Cu^o$) at the measuring electrodes in the process.

The methodical processes in accordance with the alternatives demonstrated only in principle in FIG. 1 are illustrated with reference to FIGS. 5a, 5b, on the one hand, and 6a, 6b on the other hand, and also FIG. 7. Specifically in FIGS. 5a to 6b, a hydrogel layer 35 is in each case applied above the measuring electrodes 20 and 30, which have sensor surfaces 21 and 31, said hydrogel layer enclosing capture molecules 100 for target molecules 200 situated outside the hydrogel 35. What is essential in this case is that the capture molecules 100 capture and bind the target molecules 200 and thus supply them for analysis at the sensor surface 21 and 31, respectively. With regard to this methodology, reference is made for example to applicant's earlier application PCT/DE 02/01982.

The capture molecules 100 may be for example specific thiol-modified oligonucleotides. Target molecules 200 that are intended to be bound by the capture molecules 100 are the DNAs to be analyzed.

In general, a known measuring arrangement exhibits a state in accordance with FIG. 5a, in the case of which the target DNA is present only in low concentration above the capture DNA. It is difficult in this case to attain reliable measurement results. In the case of an arrangement in accordance with FIG. 5b, by contrast, the target DNA is present in high concentration above the capture DNA, this being achieved by way of a DNA enrichment. Good measurement results can be obtained in this state.

In accordance with FIG. 6a, in addition to the complementary target DNA 200, incompletely complementary DNA fragments 200' also bind to the capture DNA. By way of a stringency treatment, non-specifically bound DNA can be selectively removed by applying respectively suitable potentials to the electrodes. The non-specifically bound DNA is then repelled on account of its weaker binding forces.

It can be seen from FIG. 1 and also subfigures 5a and 5b that a desired enrichment of the target DNA is achieved by applying specific potentials to the auxiliary electrode 40. In detail, for this purpose an auxiliary electrode 40 made of base metal, for example copper, is chosen and a positive potential is applied to the auxiliary electrode 40. If the entire arrangement is situated in an aqueous solution, $Cu^{2+}$ ions go into solution. As a result, a field gradient arises and the negatively charged DNA molecules are attracted.

Figure 7:
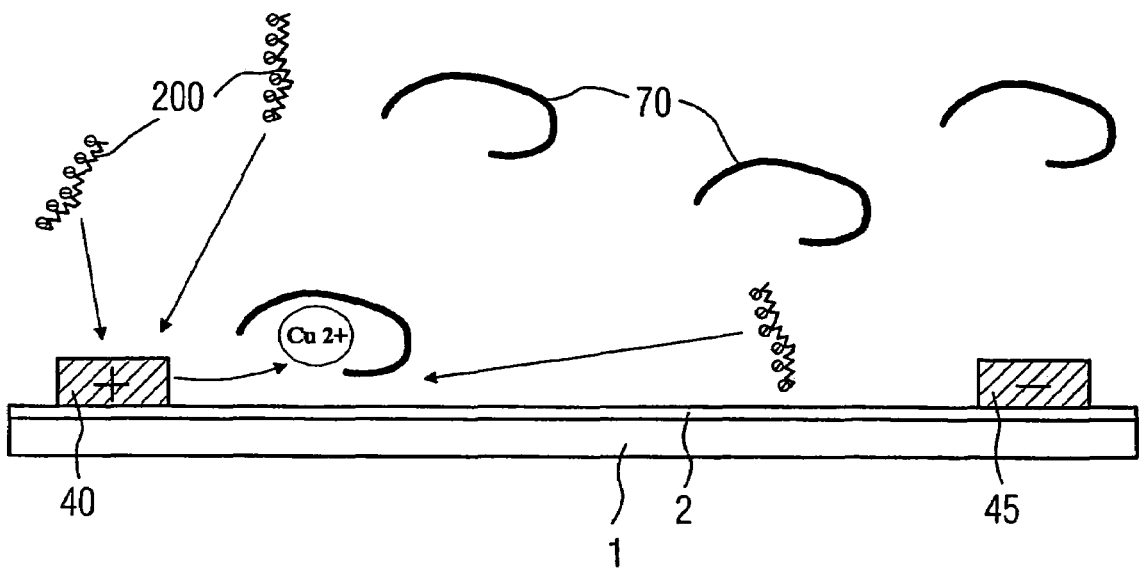
FIG. 7 shows the electrode process in the case of the invention's use of a sacrificial electrode, and also of a complexing agent.

The latter process is essentially illustrated by FIG. 7. In particular, it can be seen here that the copper ion brought into solution is complexed, for which purpose histidine molecules 70 are used.

It can be seen from FIG. 1 and also subfigures 6a and 6b that a desired selection of the DNA is achieved by applying specific potentials to the measuring electrodes 20, 30 and auxiliary electrodes 40, 45. In detail, the measuring electrodes are polarized negatively and the auxiliary electrodes positively. If the entire arrangement is situated in an aqueous solution containing copper(II) ions ($Cu^{2+}$), the latter are reduced to metallic copper ($Cu°$) on the measuring electrodes 20, 30. As a result, a field gradient arises and the negatively charged, incompletely complementary DNA is repelled.

The two alternatives may proceed separately or else in combination. Target molecules are firstly enriched and then selected. However, it is also possible to perform only a selection.

Figure 2:
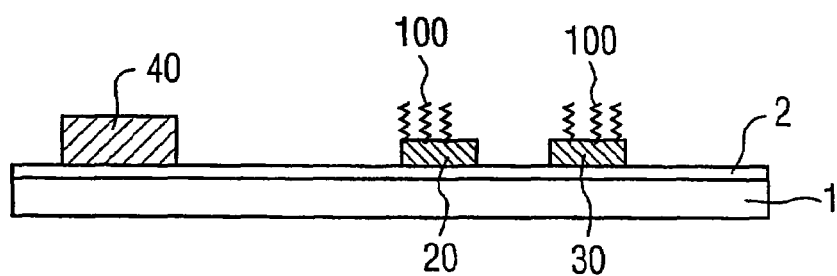
FIGS. 2 to 4 show cross sections of differently formed arrangements.
Figure 3:
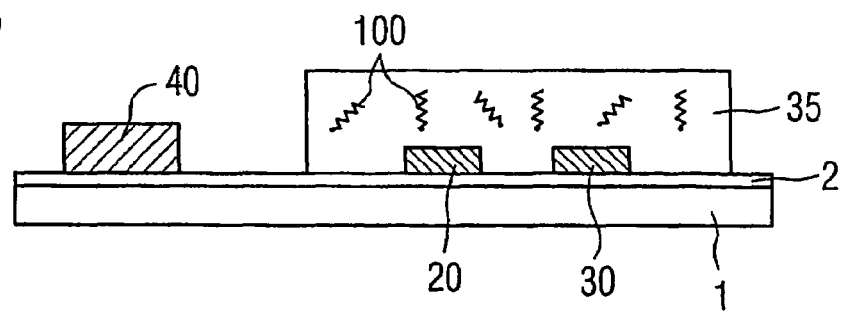
Figure 4:
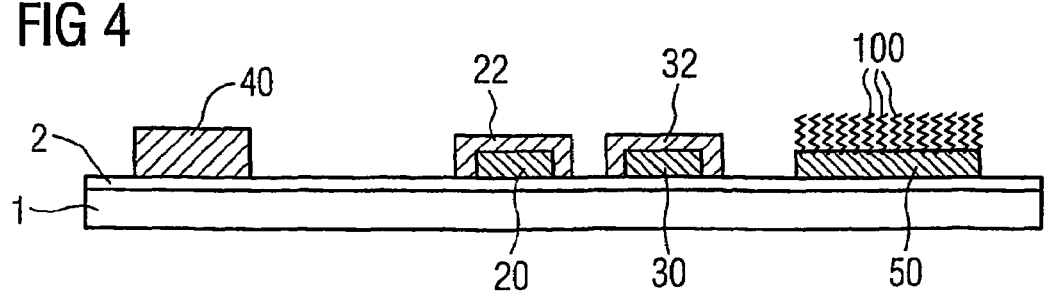

FIGS. 2 to 4 illustrate different variants of sensor arrangements. In FIG. 2, the measuring electrodes 20, 30 formed from gold have free gold sensor areas 21, 31, to which the capture DNA 100 is bound. As an alternative, a hydrogel 35 containing capture DNA 100 is present in FIG. 3.

FIG. 4 specifically illustrates an arrangement in which, besides the actual measuring electrodes 20 and 30, a free reaction area 50 made of gold is furthermore present, to which the capture DNA 100 is bound in a dense arrangement. This has the advantage of a high density of capture DNA. However, in the production of the reaction area 50, it is necessary firstly to cover the measuring electrodes 20, 30 with copper or the like in order to prevent an attachment of the catcher DNA 100 there. Copper layers 22 and 32, respectively, are present for this purpose in FIG. 4.

In all of the arrangements in accordance with FIGS. 2 to 4 the sacrificial electrode 40 is in each case arranged in the vicinity of the measuring electrodes 20 and 30 in order, as a result of copper going into solution, to build up the field gradient and thus to effect the enrichment of the target DNA 200 in the vicinity of the measuring electrodes 20 and 30. The measurement accuracy can thus be considerably improved as a result.

Figure 8:
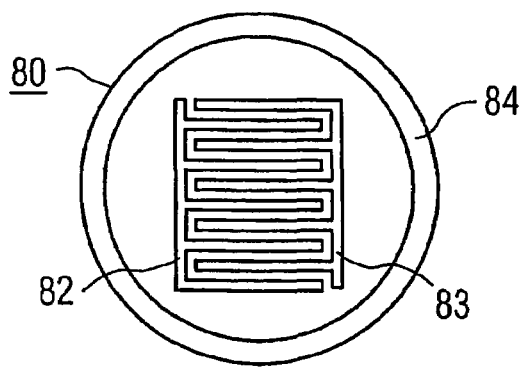
FIGS. 8 to 10 show plan views of different measuring electrode configurations.
Figure 9:
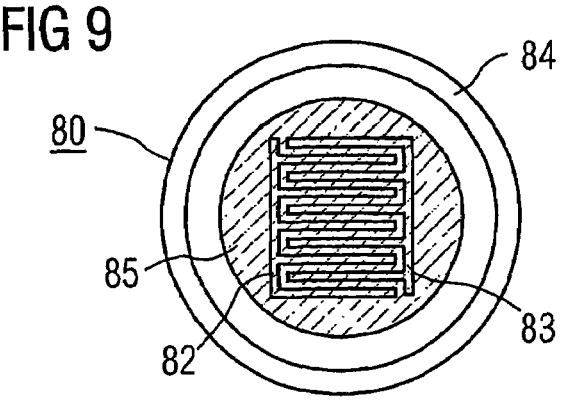
Figure 10:
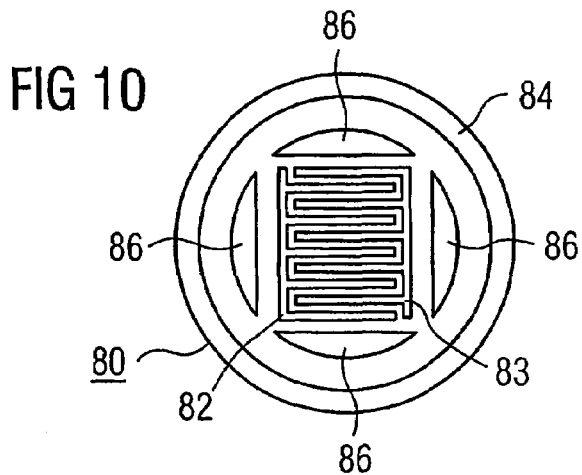

FIGS. 8 to 10 illustrate the different variants of measuring sensor in accordance with FIGS. 2 to 4 in plan view. Specifically in FIG. 8, a measuring sensor 80 is present which comprises two comb electrodes 82 and 83 with intermeshing electrode fingers, a single sacrificial electrode 84 being arranged annularly around the comb electrodes.

A corresponding arrangement emerges from FIG. 9, here the region of the comb electrodes being covered with the hydrogel layer 85. A hydrogel layer of this type may be situated over the entire measuring arrangement. Specifically in FIG. 10, reaction areas 86 for the attachment of catcher molecules are additionally present as well.

Figure 11:
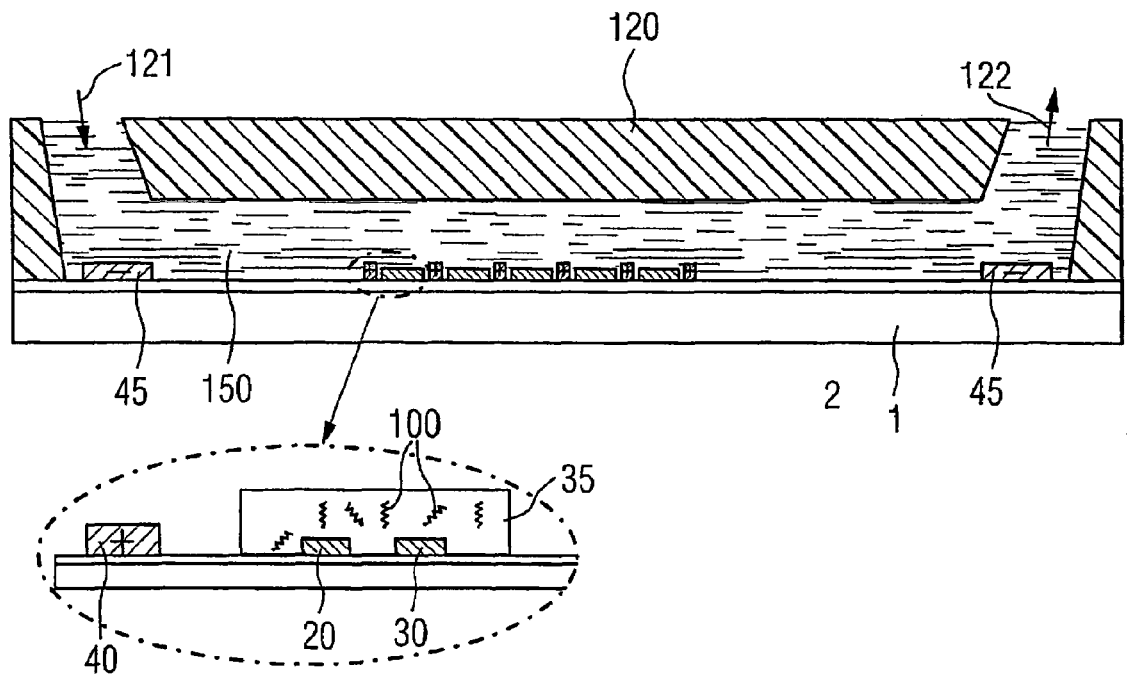
FIG. 11 shows a measuring arrangement with measuring positions arranged next to one another, in cross section.
Figure 12:
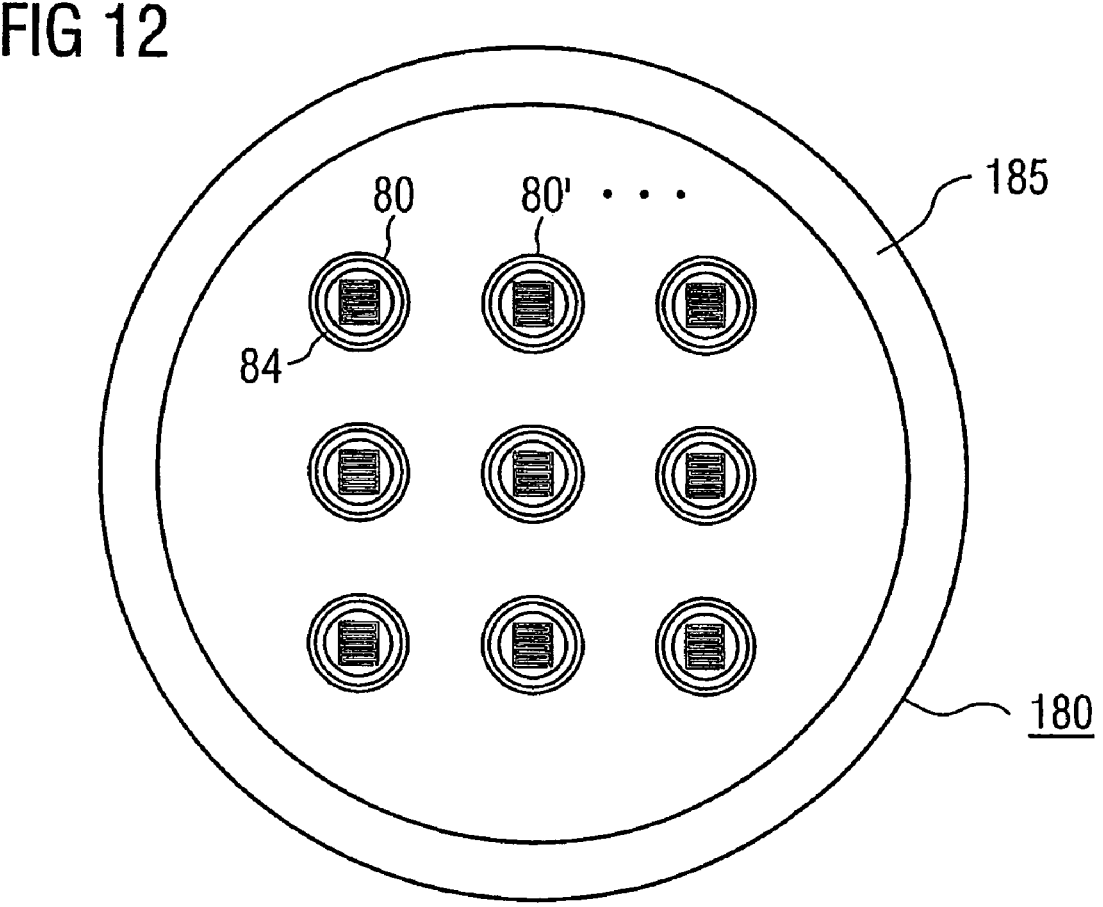
FIG. 12 shows an array arrangement formed from individual positions corresponding to FIG. 8, in plan view.

From the individual sensors in accordance with FIGS. 8 to 10 it is possible to design arrays having n rows and m columns. FIGS. 11 and 12 illustrate a complete arrangement having a multiplicity of measuring sensors 80, 80', . . . which constitute the n·m array. In this case, it is possible in principle to construct the array with individual positions corresponding to one of FIGS. 8 to 10, in the case of which each individual position has an annular copper sacrificial anode 84. In this case the auxiliary electrode 185 is arranged as a further ring around the entire n·m arrangement with the individual positions.

In accordance with FIG. 11, the complete arrangement 180 is situated in a container, e.g. a through-flow channel 150, with a cover 120, an inflow 121 and an outflow 122.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for transporting electrically charged molecules in an aqueous solution, the method comprising:
   arranging, in the vicinity of two measuring electrodes, a metallic material which is resistant in the aqueous electrolyte and is more electronegative than that of the measuring electrode, the metallic material being arranged as an electrode to which a potential can be applied; and
   bringing the metallic material, as a result of a positive potential being applied to the arranged electrode, into solution as positive ions,
   whereby negatively charged molecules are transported as target molecules in a direction of the arranged electrode to which positive potential is applied and are enriched at the measuring electrodes.

2. The method as claimed in claim 1, wherein the metal ions going into solution are complexed by the presence of a complexing agent, whereby their concentration is kept low and virtually constant.

3. The method as claimed in claim 2, wherein copper is used as the metallic material, the copper forming a copper sacrificial anode.

4. The method as claimed in claim 3, wherein histidine is used as a complexing agent for complexing the copper ion.

5. The method as claimed in claim 1, wherein catcher molecules at an electrode surface are used for detecting the target molecules.

6. The method as claimed in claim 5, wherein thiol-modified capture molecules are used as capture molecules.

7. The method as claimed in claim 5, wherein hydrogel-bound molecules are used as capture molecules.

8. The method as claimed in claim 1, wherein an electrophoresis method is performed.

9. The method as claimed in claim 8, wherein the selectivity of the process is increased by polarization of the electrodes used for the electrophoresis or DNA analysis.

10. The method as claimed in claim 1, wherein a DNA analysis of DNA fragments is effected.

11. The method as claimed in claim 10, wherein the enriched molecules are detected as target molecules during the DNA analysis.

12. The method as claimed in claim 1, wherein the measuring electrodes comprise noble metal.

13. The method as claimed in claim 12, wherein the measuring electrodes made of gold have a sensor surface to which capture molecules for the target DNA are bound.

14. The method as claimed in claim 13, wherein the measuring electrodes form an interdigital structure including comb electrodes with intermeshing electrode fingers.

15. The method as claimed in claim 12, wherein the measuring electrodes form an interdigital structure including comb electrodes with intermeshing electrode fingers.

16. The method as claimed in claim 1, wherein the metal is copper and forms a sacrificial electrode.

17. The method as claimed in claim 16, wherein the sacrificial electrode is arranged annularly around the comb electrodes.

18. The method as claimed in claim 1, wherein the measuring electrodes form an interdigital structure including comb electrodes with intermeshing electrode fingers.

19. The method as claimed in claim 18, wherein an array having m rows and n columns is formed by individual interdigital structures with sacrificial electrode.

20. The method as claimed in claim 19, wherein an auxiliary electrode with respect to the individual sacrificial electrodes runs annularly around the m·n array.

21. The method as claimed in claim 1, wherein a hydrogel layer for binding the capture molecules arranged on the measuring electrodes.

22. The method as claimed in claim 1, wherein the measuring electrodes are assigned separate reaction areas for attachment of the capture molecules.

23. The method as claimed in claim 1, wherein the method is for transporting electrically charged molecules in an aqueous solution during the operation of a DNA sensor with a redox cycling process between the two measuring electrodes.

24. The method as claimed in claim 1, wherein copper is used as the metallic material, the copper forming a copper sacrificial anode.

25. A method for binding-specific separation of electrically charged molecules in an aqueous solution, during the operation of a sensor with a cycling process between two measuring electrodes, the method comprising:
  situating metal ions in the aqueous solution;
  depositing, as a result of a negative potential being applied to the measuring electrodes, the metal ion as metal at the measuring electrodes,
  whereby negatively charged molecules bound in the vicinity of the measuring electrodes are transported away from the measuring electrodes as target molecules with a sufficiently low binding energy.

26. The method as claimed in claim 25, wherein copper is used as metal ions and gold is used as measuring electrodes.

27. The method as claimed in claim 25, wherein the molecules transported away from the measuring electrodes are those target molecules which are not intended to be detected during a DNA analysis.

* * * * *